United States Patent [19]

Mettes et al.

[11] Patent Number: 5,054,309
[45] Date of Patent: Oct. 8, 1991

[54] PROCESS FOR PRODUCING LOW-CONCENTRATION GAS MIXTURES, AND APPARATUS FOR PRODUCING THE SAME

[75] Inventors: Jacques Mettes, Doylestown, Pa.; Takako Kimura, Toyosato, Japan; Michael Schack, Dusseldorf, Fed. Rep. of Germany

[73] Assignee: L'Air Liquide, Societe Anonyme Pour L'Etude et L'Exploitation des Procedes Georges Claude, Paris, France

[21] Appl. No.: 437,615

[22] Filed: Nov. 17, 1989

[30] Foreign Application Priority Data

Nov. 21, 1988 [EP] European Pat. Off. ....... 88.402920.8

[51] Int. Cl.⁵ .......................................... G01N 33/00
[52] U.S. Cl. ............................................ 73/1 G; 137/7
[58] Field of Search .................. 73/1 G; 137/3, 7; 366/101, 106, 107

[56] References Cited

U.S. PATENT DOCUMENTS

| | | | |
|---|---|---|---|
| 3,242,715 | 3/1966 | Hüsner | 73/1 G |
| 3,298,383 | 1/1967 | Cooper | 137/3 |
| 3,359,784 | 12/1967 | Jorre et al. | 73/1 G |
| 3,449,958 | 6/1969 | Bailey | 73/1 G X |
| 3,533,272 | 10/1970 | Dahms . | |
| 3,776,023 | 12/1973 | Budd et al. | 73/1 G |
| 3,833,016 | 9/1974 | Lucero et al. | 137/340 |
| 3,875,499 | 4/1975 | Roberts | 73/40.7 X |
| 3,998,239 | 12/1976 | Kruishaop | 137/101.11 |
| 4,012,301 | 3/1977 | Rich et al. | 204/157.9 X |
| 4,474,590 | 10/1984 | Bucchianeri | 62/18 X |
| 4,977,776 | 12/1990 | Shindo et al. | 73/1 G |

FOREIGN PATENT DOCUMENTS

| | | | |
|---|---|---|---|
| 811973 | 5/1969 | Canada | 73/1 G |
| 1548880 | 10/1969 | Fed. Rep. of Germany . | |
| 2904872 | 8/1980 | Fed. Rep. of Germany . | |
| 2321122 | 3/1977 | France . | |
| 6800 | 2/1972 | Japan | 73/1 G |
| 173740 | 10/1982 | Japan | 73/1 G |
| 60-143738 | 7/1985 | Japan . | |
| 1281984 | 1/1987 | U.S.S.R. | 73/1 G |
| 1491190 | 11/1977 | United Kingdom | 73/1 G UX |
| 2040715 | 9/1980 | United Kingdom . | |

Primary Examiner—Tom Noland
Attorney, Agent, or Firm—Oblon, Spivak, McClelland, Maier & Neustadt, P.C.

[57] ABSTRACT

This invention relates to a process for producing gas mixtures by a plurality of dilution steps of a high concentration standard gas with a high purity diluent gas. According to the invention, as soon as the high purity diluent gas is generated, no further contaminants such as gaseous impurities are added during the further mixing of diluting steps of the process. Only orifices or needle valves are used in the mixing or diluting lines while mass flow controllers and pressure regulators are placed upstream, at the output of the gas sources and/or downstream, i.e. in the gas-venting lines. The invention particularly applies to trace analysis of gas with Atmospheric Pressure Ionization Mass Spectrometry.

17 Claims, 2 Drawing Sheets

PROCESS FOR PRODUCING LOW-CONCENTRATION GAS MIXTURES, AND APPARATUS FOR PRODUCING THE SAME

FIELD OF THE INVENTION

The present invention relates to the manufacture of low-concentration gas mixtures and, more particularly, to a process and an apparatus for producing gas mixtures by diluting a material gas in one or more stages, for testing, calibrating, . . . highly sensitive analytical instruments, such as those used for sub-ppb analysis with Atmospheric Pressure Ionization Mass Spectrometry (APIMS).

BACKGROUND OF THE INVENTION

A variety of gases are used in manufacturing semiconductor devices such as LSIs. These gases contain impurities. These impurities have been suspected to have an adverse influence on the characteristics of the LSIs. Hence, it is demanded that the gases be as pure as possible This demand grows stronger, along with the increase in the integration density of LSIs. To meet this demand, a high-accuracy and reliable analysis of gases is required The techniques commonly used for analyzing such gases for determining the impurity contents thereof are: gas chromatography (GC), gas chromatography-mass spectroscopy (GC-MS), and Fourier transformed infrared spectroscopy (FTIR). The detection limit of these techniques are, however, 1 to 10 ppb at best. In view of this, these analytical techniques cannot be said to determine the impurity content of the gases as sensitively as is required in the manufacture of LSIs.

Furthermore, in order to conduct a successful quantitative analysis on a particular species in a sample gas by a non-absolute method such as mass spectroscopic method, it is necessary to make a calibration curve by using standard gas mixtures containing the species to be analysed. Theses standard mixtures can be prepared by diluting a gas mixture of a known high concentration of the impurity, with a diluent gas. The concentration of the species in the final mixture should be preferably in the same range as that in the sample gas to be analyzed. When the concentration of the sample gas is very low, the following factors determine the accuracy of the analysis a. Detection limit of the analytical instrument
b. Purity of the diluent gas
c. Mixing techniques When the detection limit of the analytical instrument is in lower orders, it is difficult to obtain factors b and c, both in the comparable orders.

Recently, a highly sensitive analytical instrument, which is called atmospheric-pressure ionization mass spectrometer (APIMS) has been developed. This instrument can determine the contents of molecular species down to 10 ppt. Therefore, it has become desirable to produce standard gas mixtures in the low concentration range.

Low-concentration standard gas mixtures, which is used as a calibration gas in analyzing extremely pure gases, could be produced by diluting a high-concentration standard gas in one or a plurality of stages. In order to produce a low-concentration standard gas, continuously at a desired flow rate and pressure, the two-stage dilution method, for example, is employed In this method, first the high-concentration standard gas is diluted with a diluent gas of the same kind of the sample gas to a predetermined medium lower concentration, then most of this medium concentration mixture is discarded, and the remaining fraction of said gas is further diluted with the diluent gas. The concentration of the species within this low concentration, final standard gas must be controlled accurately. For this purpose, various devices such as mass flow controllers, pressure regulator, . . . must be used to control the flow rates of the material gas and the diluent gases. As soon as low concentrations should be made of species that make part of our natural environment, the use of regulation devices like mass flow controllers, pressure regulators, etc. . . . would give serious limitations on the lower limits that can be achieved.

SUMMARY OF THE INVENTION

In order to prepare low-concentration standard gas mixtures in dynamic mode, the inventors have found that it is very important to maintain the diluent gas lines and the mixing lines free from contamination. The devices necessarily used to control the flow rates and pressures of the material gas and the diluent gas absorb and degas contaminants and are unavoidably sources of contaminants. The contaminants, if released from these devices, greatly change the concentration of the low-concentration standard gas mixture or add additional species in an uncontrolled manner. Consequently, no correct calibration curves can be obtained Without correct calibration curves, even a high-accuracy analytical instrument such as an APIMS cannot analyze gases with such an accuracy as is required now in manufacturing LSIs.

One object of the present invention is to provide a process for producing low-concentration gas mixtures desirable as standard gas mixtures for analyzing high-purity gases, in which diluent gas lines and mixing lines are maintained free from contamination.

Another object of the invention is to provide an apparatus for performing the process efficiently, thereby producing such low-concentration gas mixtures.

According to the present invention, there is provided a process for producing low-concentration gas mixtures, comprising the steps of controlling the pressure of a raw gas; purifying the raw gas, thereby generating a high-purity diluent gas; dividing said high purity diluent gas in a first and second portions, controlling the flow rate of a high-concentration standard gas mixing said first portion of said high-purity diluent gas and the high-concentration standard gas, thereby generating a medium-concentration standard gas, dividing the medium-concentration gas mixture into a first flow and a second flow; diluting the gas mixture of the first flow with said second portion of the high-purity diluent gas, thereby generating a low-concentration gas mixture; controlling the pressure of said second flow of the medium concentration gas mixture; and controlling the pressure of said low concentration gas mixture.

According to a preferred embodiment of the invention and unless it is recovered or recycled, the second flow of the medium concentration gas mixture is generally vented.

Other embodiments of the process of the invention are provided according to any one of claims 2 to 12.

Further, according to the invention, there is provided an apparatus for producing low-concentration gas mixtures, comprising: means for controlling the pressure of a raw gas; means for purifying the raw gas, thereby generating a high-purity diluent gas means for dividing said high purity diluent gas in a first and second portion, said second portion flowing through first restricting means; second restricting means through which said first portion flows; means for controlling the flow rate of a high-concentration standard gas; means for mixing the first portion of the high-purity diluent gas and the high-concentration standard gas, thereby generating a medium-concentration gas mixture; means for dividing the medium-concentration gas mixture into a first flow and a second flow said first flow passing through third restricting means; means for diluting the gas mixture of the first flow with the second portion of the high purity diluent gas, thereby generating a low-concentration gas mixture; means for controlling the pressure of said second flow of the gas mixture thereby controlling the pressure of said low concentration gas mixture.

The basic concept of the present invention is to provide a process and related apparatus wherein, as soon as the high purity diluent gas is generated, no further contaminants such as particles and/or gaseous impurities, . . . are added during the further mixing and/or diluting steps of the process. That means that all the devices used for carrying out those steps are able to generate no additional contaminants. Those devices are generally selected among pipes, such as electropolished pipes, and restriction means, such as needle valves (controllable flowrate), calibrated orifices, small diameter pipes, with appropriate diameters as well as appropriate ratios of diameters when different flow-rates and pressures have to be handled in different lines, the selection of the appropriate ratio of diameters being well-known by the man skilled in the art.

The present invention can be applied to a multi-stage diluting process, wherein a zero gas, i.e., a high-purity diluent gas to be mixed divided into n flow portions, these flow portions of the zero gas being sequentially added to a mixture gas such that the nth flow of the zero gas is added to a portion of the gas mixture diluted in the $(n-1)$th stage.

This multi-stage diluting process comprises the steps of: controlling the pressure of a raw gas; purifying the raw gas, thereby generating a high-purity diluent gas; dividing the high-purity diluent gas into n flow portions; controlling the flow rate of a high-concentration standard gas; mixing a first flow portion of the high-purity diluent gas with the high-concentration standard gas, thereby generating a first medium-concentration gas mixture; dividing the first medium-concentration gas mixture into a first flow and a second flow; mixing said first flow of said first medium-concentration gas mixture with a second flow portion of the high-purity diluent gas, thereby generating a second medium concentration gas mixture; dividing said second medium concentration gas mixture into a first flow and a second flow; repeating the two above mentioned mixing and dividing steps to generate a first flow and a second flow of a $(n-1)$th medium concentration gas mixture; mixing the first flow of the $(n-1)$th medium-concentration gas mixture with the nth flow portion of the high purity diluent gas, thereby generating a low concentration gas mixture; and controlling the pressure of the second flow of each of the first to $(n-1)$th medium-concentration gas mixtures, the pressure of said second flow of the $(m)$th medium concentration gas mixture ($1 < m < n-1$) being smaller than that of the $(m-1)$th medium concentration gas mixture. Preferably, if it is not recovered or recycled, the second flow of each of the medium concentration gas mixture is vented.

Still further, according to the invention there is provided an apparatus for producing low-concentration gas mixtures, comprising: means for controlling the pressure of a raw gas; means for purifying the raw gas, thereby generating a high-purity diluent gas means for dividing said high-purity diluent gas into n flow portions, each portion flowing through first restricting means; means for controlling the flow rate of a high-concentration standard gas; means for mixing a first flow-portion of the high-purity diluent gas with the high-concentration standard gas, thereby generating a first medium-concentration gas mixture; means for dividing the first medium-concentration gas mixture into a first flow and a second flow, said first flow passing through second restriction means; means for mixing said first flow of the first medium-concentration gas mixture with a second flow portion of the high-purity diluent gas, thereby generating a second medium concentration gas mixture; means for dividing said second medium-concentration gas mixture into a first flow and a second flow; means for mixing and means for dividing to generate a first flow and a second flow of a $(m)$th medium concentration gas mixture with $1 < m < n-1$, means for mixing the first flow of the $(n-1)$th flow of the medium-concentration gas mixture with the nth flow portion of the high-purity diluent gas, generating a low concentration gas mixture; means for controlling the pressure of said low concentration gas mixture; means for controlling the pressure of the second flow of each of the first to $(n-1)$th medium-concentration gas mixtures.

Preferably, the apparatus according to the invention will further comprises, means for venting the second flow of each of the medium-concentration gas mixtures Alternatively, it may comprise means for recovering or recycling said second flow of each of the medium concentration gas mixtures.

No devices which might potentially be contaminant sources are used in the zero gas lines or the mixing lines in the process or apparatus according to the present invention. Orifices or needle valves, which are not contaminant sources, are generally used in the zero gas lines or mixing lines. In the conventional prior art process and apparatus, mass flow controllers and pressure regulators are placed in the zero gas lines and the mixing lines in order to control the flow rates and pressures of the low-concentration gas mixture. According to the present invention, mass flow controllers and pressure regulators are placed upstream of the gas-purifying means, in the high-concentration standard gas lines, the contamination of which is not so problematical, and in the gas-venting lines which are downstream the gas lines of the system according to the invention which are thus prevent from contamination. This specific arrangement of the mass flow controllers and the pressure regulators is based on the inventors' finding that the controllers and regulators can control correctly the flow rate and pressure of the low-concentration gas mixture.

In the body of the present specification, various steps are defined which may have the following meanings according to the invention:

Controlling the pressure of the raw gas is preferably carried out either before the purification step, by means of a pressure regulator or after the purification step, by means of a back pressure regulator.

Controlling the flow rate of a high concentration standard gas may be preferably accurately carried out either by means of a mass flow controller or a neddle valve associated to a pressure regulator.

Controlling the pressure of the low concentration gas mixture, i.e. the mixture adapted to flow in the analyzer, such as APIMS, is carried out preferably:

with a back pressure regulator connected at the end of the pipe delivering the low concentration gas mixture, thus avoiding about any contamination of the pipe.

with the analysis apparatus itself which is sometimes able to control itself said pressure (e.g. when the analysis is carried out at atmospheric pressure)

with a pressure regulator connected at the output of the analysis apparatus, thus providing no contamination of the low concentration gas mixture.

In the present specification the terms high purity diluent gas or zero gas are equivalent. Such high purity gas is obtained by well-known techniques such as catylisis, chemical conversion, gettering, ambient temperature physical absorption, cryogenic absorption, filtering with molecular sieves, . . . or a combinaison of those methods, in order to remove about any impurities such as particles and gaseous impurities, . . .

Various appropriate methods are disclosed for example in the article of F. W. Giaccobbe and G. S. Khan, both of American Air Liquide Inc., entilted "Production of ultra high purity nitrogen"—Solid state Technology-July 1987.

It is also to be understood that a high concentration standard gas means preferably a gas containing only one species. But according to the invention, it also means a mixture of a plurality of species, whatever the relative proportions of each species are.

BRIEF DESCRIPTION OF THE DRAWING FIGURES

This invention will be more fully understood from the following detailed description when taken in conjunction with the accompanying drawings, in which:

FIG. 1 is a flow diagram showing a process of producing low-concentration gas mixtures, in which a high-concentration standard gas is diluted in two stages; and FIG. 2 is also a flow diagram showing a process of producing a low-concentration gas mixture, in which a high-concentration standard gas is diluted in n stages.

DETAILED DESCRIPTION

A variety of embodiments of the present invention will now be described, with reference to the accompanying drawings.

Figure 1:
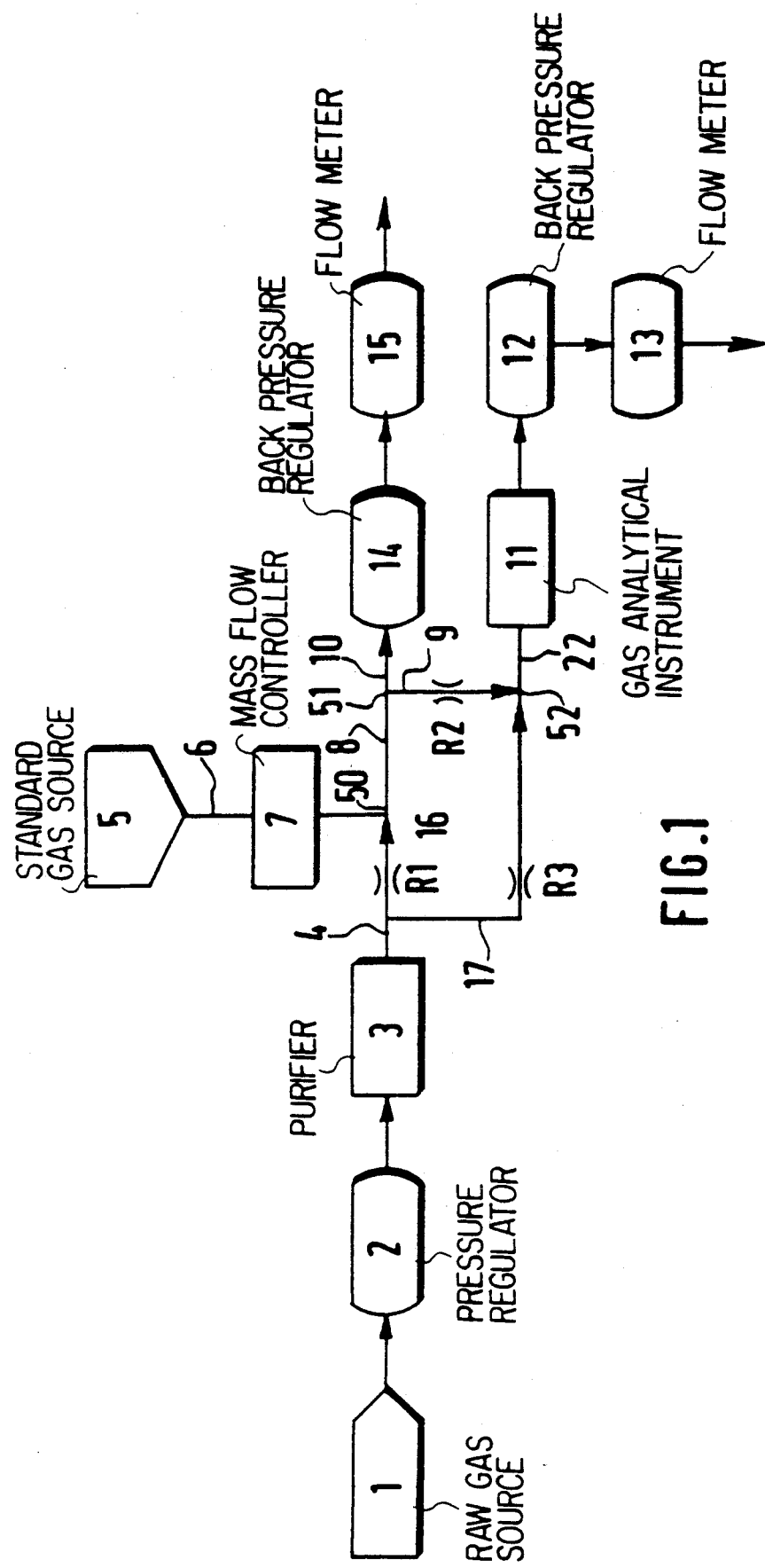

FIG. 1 is a flow diagram showing a process for producing low-concentration gas mixtures, wherein a high-concentration standard gas is diluted in two stages. As is shown in FIG. 1 the raw gas is supplied from a raw gas source 1 via a pressure regulator 2 to a purifier 3. The output gas from purifier 3, i.e., zero gas, is divided by the branching tube 4 into a first zero-gas portion 16 and a second zero-gas portion 17. The first zero-gas portion 16 passes through a restriction device R1 such as an orifice or a needle valve, and is mixed with a high-concentration standard gas 6 supplied from a standard gas source 5, through the mass flow controller 7 and the T-junction 50 thus diluting this gas mixture 6. As a result, a medium-concentration gas mixture 8 is prepared. The flow rate of the high-concentration standard gas mixture 6 is controlled by the mass flow controller 7 connected to the output of the standard gas source 5.

The medium-concentration gas mixture 8 is divided in the branching tube 51 into a first and a second streams 9 and 10. The ratio of the flow rates of the streams 9 and 10 is, for example, 1:100. This ratio can be reasonnably varied between about 1:20 and 1:500 (the range of the ratio is limited by the measurement accuracy of the two flow rates).

The first stream 9 of the gas mixture 8 is supplied through the restriction device R2 which is preferably either an orifice or a needle valve. Meanwhile the second zero-gas portion 17 is supplied via the restriction device R3 (either an orifice or a needle valve), and is mixed in the branching tube 52 with the first stream 9 of the gas mixture 8, thus diluting the medium concentration gas mixture to generate a low-concentration gas mixture 22. As a result, a standard gas mixture 22 having a low concentration is prepared. This standard gas mixture can be used for various purposes. For example, it is supplied to a gas analytical instrument 11.

The pressure of the low-concentration gas mixture 22 can be controlled by means of a back pressure regulator 12 connected to the outlet port of the instrument 11, or by opening the outlet port of the instrument 11 to the atmosphere. In either cases, the flowmeter 13 measures the flow rate of the low-concentration gas mixture 22 before this gas mixture is discarded out of the system.

In the meantime, the second stream 10 is discarded through the back-pressure regulator 14 and the flowmeter 15. The back-pressure regulator 14 is used to adjust the upstream pressure of the gas mixture 8.

Figure 2:
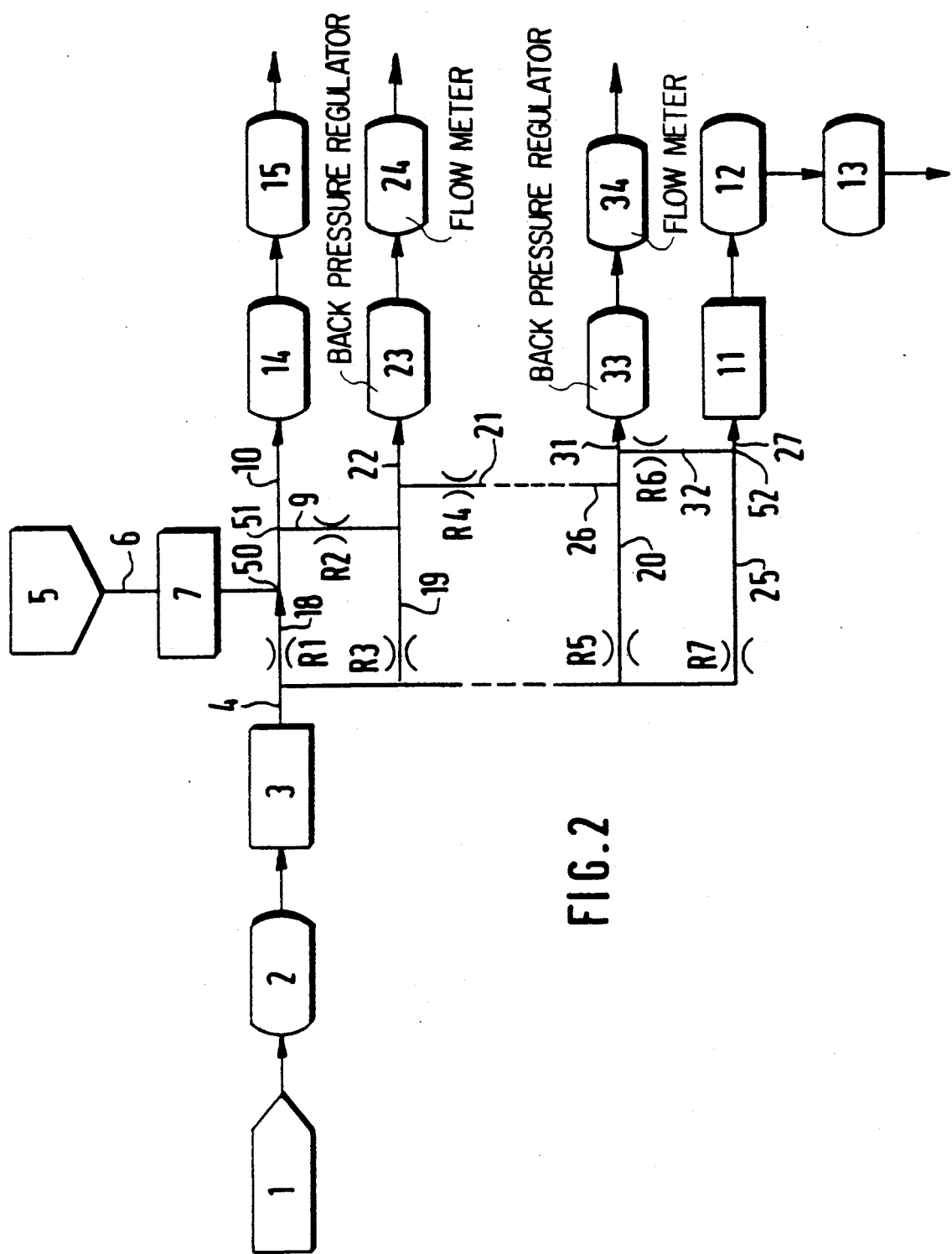

FIG. 2 is a flow diagram showing a process for producing low-concentration gas mixtures, in which a high-concentration standard gas is diluted in n stages. The same devices of FIG. 1 bear the same references. As is shown on FIG. 2, the zero gas 4 is divided into a first, second, . . . n−1 and an zero-gas portions 18, 19, . . . , 20 and 23. The first flow 21 of the medium-concentration gas mixture, which has been prepared in the second dilution stage, (but which is not yet a low-concentration gas mixture according to the present embodiment) is diluted with a third zero-gas portion, etc. . . . up to obtain the first flow of the (n−2) medium-concentration gas mixture 26. The second flow 22 of the medium concentration gas mixture, which has been prepared in the second dilution stage, is discarded through the back-pressure regulator 23 and the flow-meter 24, thereby adjusting the upstream pressure with the regulator 23. The restriction devices R1 to R7, all shown on FIG. 2, are each either an orifice or a needle valve. The said first flow 26 is diluted with the (n−1) zero-gas portion 20, generating the (n−1) medium-concentration gas mixture which is divided in a first flow 32 and a second flow 31, said second flow 31 being vented through the back pressure regulator 33 and the flow meter 34. The said first flow 32 is further diluted in the branching tube 52 with the n zero gas portion 25 (or nth flow portion) generating the low-concentration gas mixture 27 introduced in the analyzer 11 as explained on FIG. 1.

The present invention is not limited to the embodiments which are shown on FIGS. 1 and 2 which have been described above. As explained above, in the process for producing a low-concentration gas mixtures according to the present invention, no potential contaminant sources are used which are connected to the zero gas lines or mixing lines which are located downstream of the purifier. Hence, the process according to the invention can produce low-concentration gas mixtures which have a desired accurate concentration of one or several species in a raw gas.

We claim:

1. A process for producing low-concentration gas mixtures, comprising the steps of:
   controlling the pressure of a raw gas;
   purifying the raw gas, thereby generating a high purity diluent gas;
   dividing said high purity diluent gas into first and second portions;
   controlling the flow rate of at least one high-concentration standard gas;
   mixing said first portion of said high-purity diluent gas and the high-concentration standard gas, thereby generating a medium-concentration gas mixture;
   dividing the medium-concentration gas mixture into a first flow and a second flow;
   diluting the gas mixture of the first flow with said second portion of the high purity diluent gas, thereby generating a low-concentration gas mixture;
   controlling both the pressure of said second flow of the medium gas mixture and the the pressure of said low concentration gas mixture downstream of their creation.

2. The process according to claim 1, further comprising the step of restricting the flow of the first portion of the high-purity diluent gas to be mixed with the high-concentration standard gas.

3. The process according to claim 2 wherein the step of restricting the flow is carried out by restriction means.

4. The process according to claim 1 or 2, further comprising the step of restricting said first flow of the medium-concentration gas mixture.

5. The process according to claim 1, further comprising the step of restricting the flow of said second portion of the high-purity diluent gas.

6. The process according to claim 1, further comprising the step of venting said second flow of medium concentration gas mixture.

7. A process for producing low-concentration gas mixtures, comprising the steps of:
   controlling the pressure of a raw gas;
   purifying the raw gas, thereby generating a high purity diluent gas;
   dividing said high purity diluent gas into first and second portions;
   controlling the flow rate of at least one high-concentration standard gas;
   mixing said first portion of said high-purity diluent gas and the high-concentration standard gas, thereby generating a medium-concentration gas mixture;
   dividing the medium-concentration gas mixture into a first flow and a second flow;
   mixing said first flow of said medium-concentration gas mixture with a second flow portion of the high-purity diluent gas, thereby generating a second medium-concentration gas mixture;
   dividing said second medium-concentration gas mixture into a first flow and a second flow;
   repeating (m) times the two above mentioned mixing and dividing steps to generate a first and a second flow of a (m)th medium-concentration gas mixture, with m varying from 2 to n−1;
   mixing the first flow of the (n−1)th flow of the (n−1)th flow of the medium-concentration gas with the nth flow portion of the high-purity diluent gas, thereby generating a low-concentration gas mixture;
   controlling both the pressure of said low-concentration gas mixture; and
   the pressure of the second flow of each of the first to (n−1)th medium-concentration gas mixtures downstream from their creation, the pressure of said second flow of the (m)th medium-concentration gas mixture ($1<m<n-1$) being smaller than that of the (m−1)the medium-concentration gas mixture.

8. The process according to claim 7, further comprising the step of restricting the flow of each of the n flow portions of the high purity diluent gas.

9. The process according to claim 8, wherein the step of restricting the flow is carried out by plural restriction means.

10. The process according to claim 7 or 8, further comprising the step of restricting the flow of said first flow of each of said medium-concentration gas mixtures.

11. The process according to claim 1 or 7, further comprising the steps of controlling the flowrate of a plurality of high concentration standard gases and mixing said high concentration standard gases to generate a high concentration standard gas mixture of which respective proportions by volume are controlled, said high concentration mixture being further mixed with said first portion of said high purity diluent gas.

12. The process according to claim 7 further comprising the step of venting the second flow of each of the medium-concentration gas mixtures.

13. An apparatus for producing low-concentration gas mixtures, comprising:
   gas line means;
   means for controlling the pressure (2) of a raw gas;
   means for purifying the raw gas (3), thereby generating a high-purity diluent gas;
   means for dividing (4) said high-purity diluent gas into a first and a second portion, said second portion flowing through first restricting means (R1);
   second restricting means (R3) through which said first portion flows;
   means for controlling the flow rate (7) of a high-concentration standard gas;
   means for mixing (50) the first portion of the high-purity diluent gas and the high-concentration standard gas, thereby generating a medium-concentration gas mixture;
   means for dividing (51) the medium-concentration gas mixture into a first flow and a second flow, said first flow passing through third restriction means (R2);
   means for diluting (52) the gas mixture of the first flow with said second portion of the high-purity diluent gas, thereby generating a low-concentration gas mixture;
   both means for controlling the pressure (14,15) of said second flow portion of the gas mixture, thereby controlling the pressure of said first portion and
   means for controlling the pressure (12,13) of said low-concentration gas mixture positioned downstream of the gas line means.

14. The apparatus according to claim 13, characterized in that each restricting means is an element of the group consisting of calibrated orifices and needle valves.

15. An apparatus for producing low-concentration gas mixtures comprising:
   gas line means;
   means for controlling the pressure (2) of a raw gas;
   means for purifying the raw gas (3), thereby generating a high-purity diluent gas;
   means for dividing (4) said high-purity diluent gas into n flow portions, each respective portion flowing through a respective first restricting means (R1, R3, R5, R7);
   means for controlling the flow rate (7) of a high-concentration standard gas;
   means for mixing (50) a first flow portion of the high-purity diluent gas with the high concentration standard gas, thereby generating a first medium-concentration gas mixture;
   means for dividing (51) the first medium-concentration gas mixture into a first flow and a second flow, said first flow passing through second restriction means (R2);
   means for mixing said first flow of the first medium-concentration gas mixture with a second flow portion of the high-purity diluent gas, thereby generating a second medium-concentration gas mixture;
   means for dividing said second medium-concentration gas mixture into a first flow and a second flow;
   means for mixing and means for dividing to generate a first flow and a second flow of a $(n-1)$th medium-concentration gas mixture;
   means for mixing (52) the first flow of the $(n-1)$th flow of the medium-concentration gas with the nth flow portion of the high-purity diluent gas, thereby generating a low-concentration gas mixture;
   both means for controlling the pressure (12, 13) of said low concentration gas mixture and
   means for controlling the pressure (14, 15, 23, 24, 33, 34) of the second flow of each of the first to $(n-1)$th medium-concentration gas mixtures positioned downstream of the gas line means.

16. The apparatus according to claim 15, wherein the first and second flow-restricting means are each an element of the group consisting of calibrated orifices and needle valves.

17. The apparatus according to claim 15 or 16, further comprising means for venting the second flow of each of the medium-concentration gas mixtures.

* * * * *